US010305692B2

(12) United States Patent
Peterson

(10) Patent No.: US 10,305,692 B2
(45) Date of Patent: May 28, 2019

(54) PAIRING OF DEVICES FOR FAR-FIELD WIRELESS COMMUNICATION

(71) Applicant: Medtronic, Inc., Minneapolis, MN (US)

(72) Inventor: Erik J. Peterson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 138 days.

(21) Appl. No.: 15/439,503

(22) Filed: Feb. 22, 2017

(65) Prior Publication Data
US 2018/0241564 A1 Aug. 23, 2018

(51) Int. Cl.
| | |
|---|---|
| *H04L 9/00* | (2006.01) |
| *H04L 9/32* | (2006.01) |
| *H04L 9/14* | (2006.01) |
| *H04L 9/30* | (2006.01) |
| *A61M 31/00* | (2006.01) |
| *A61N 1/36* | (2006.01) |
| *A61N 1/378* | (2006.01) |
| *A61N 1/372* | (2006.01) |

(Continued)

(52) U.S. Cl.
CPC ......... *H04L 9/3236* (2013.01); *A61M 31/002* (2013.01); *A61N 1/3605* (2013.01); *A61N 1/3787* (2013.01); *A61N 1/37223* (2013.01); *H04L 9/14* (2013.01); *H04L 9/30* (2013.01); *H04W 76/10* (2018.02); *A61M 2205/3523* (2013.01); *A61M 2205/8206* (2013.01); *A61M 2205/8243* (2013.01); *H04L 2209/80* (2013.01); *H04L 2209/88* (2013.01); *H04W 4/80* (2018.02)

(58) Field of Classification Search
None
See application file for complete search history.

(56) References Cited

U.S. PATENT DOCUMENTS

| | | |
|---|---|---|
| 8,432,260 B2 | 4/2013 | Talty et al. |
| 8,768,251 B2 | 7/2014 | Claus et al. |
| 2003/0114897 A1 | 6/2003 | Von Arx et al. |

(Continued)

OTHER PUBLICATIONS

"Bluetooth Core Specification v5.0, Section 5, Security Overview," Bluetooth Special Interest Group (SIG), Dec. 6, 2016, pp. 240-251.

(Continued)

*Primary Examiner* — Beemnet W Dada
(74) *Attorney, Agent, or Firm* — Shumaker & Sieffert, P.A.

(57) ABSTRACT

In one example, a method includes transitioning, responsive to determining that a charging coil of wireless charger is in proximity of an implantable medical device (IMD) and by the IMD, from operating in a non-pairing mode into a pairing mode of a far-field wireless communication protocol. In this example, operating in the paring mode comprises: receiving, by the IMD and via a transceiver of the far-field wireless communication protocol, a public encryption key from another device that is different than the wireless charger; and determining, based on the public encryption key of the other device and a public encryption key of the IMD, a link encryption key for future communication between the IMD and the other device. In this example, the method further includes communicating, by the IMD and based on the link encryption key, with the other device via the far-field wireless communication protocol.

20 Claims, 4 Drawing Sheets

(51) Int. Cl.
   *H04W 76/10* (2018.01)
   *H04W 4/80* (2018.01)

(56) References Cited

U.S. PATENT DOCUMENTS

| | | |
|---|---|---|
| 2008/0057868 A1 | 3/2008 | Chang |
| 2014/0221767 A1 | 8/2014 | Olson et al. |
| 2016/0330573 A1* | 11/2016 | Masoud .................. H04W 4/90 |

OTHER PUBLICATIONS

"Clinician's Manual," Implantable Pulse Generator Proclaim™ IPG, St. Jude Medical, Apr. 2016, 24 pp.

* cited by examiner

PAIRING OF DEVICES FOR FAR-FIELD WIRELESS COMMUNICATION

GOVERNMENT INTEREST

This invention was made with government interest under prime award number N66001-15-C-4014, sub-award number RES509889 awarded by DARPA. The government has certain rights in the invention.

TECHNICAL FIELD

The disclosure relates to medical device communication and, more particularly, encrypting communications to or from medical devices.

BACKGROUND

A computing device may be configured to transmit communications to, and receive communications from, other computing devices. These communications may include data or any information that is transmitted between devices either wirelessly or via a wired connection. Communications that are public or otherwise do not include sensitive information may be unsecured. Communications that are intended to be private to two or more devices may be encrypted such that the information contained therein is not readily available to unauthorized devices.

In some examples, communications between an external device (e.g., a medical device programmer or data acquisition device) and an implantable medical device (e.g., a pacemaker, a defibrillator, a neurostimulator, a sensor, or a drug pump) may be encrypted to secure sensitive information such as collected patient data or programming instructions that at least partially define the operation of an implantable medical device. Secure communication involving medical devices may involve an encryption scheme known to both the external device and the implantable medical device. For example, both the external device and the implantable medical device may utilize a stored encryption key to encrypt and/or decrypt some or all information transmitted between the devices.

Implantable medical devices including those that are positioned on the exterior of a body of a patient as well as those that are positioned subcutaneously or deeper typically utilize an on-board battery that allows the patient to be untethered to a power source. The patient maintains mobility while the implantable medical device performs a particular medical task by operating on power from the battery. For instance, the implantable medical device may provide electrical stimulation therapy for neurological or cardiac conditions, may provide drug delivery for various conditions such as pain management, and/or may provide physiological monitoring.

While the on-board battery may power the medical device for a relatively long period of time, the on-board battery will eventually be depleted. Prior to rechargeable medical systems, the implantable medical device would be replaced once the battery became depleted. With rechargeable medical systems, an external device (i.e., a wireless charger) provides recharge energy over a proximity coupling, which is typically inductive, to the implantable medical device. This recharge energy restores the on-board battery to a satisfactory level for continued operation of the medical device.

SUMMARY

In general, the disclosure is directed to devices, systems, and techniques for secure wireless communication between two devices (e.g., a medical device programmer and an implantable medical device) using a far-field communication protocol, such as a Bluetooth communication protocol. Prior to secure communication, the two devices may perform a pairing procedure. The devices may perform the pairing procedure while operating in a pairing mode. During the pairing procedure, the devices may each generate an encryption key (e.g., a link encryption key) based on respective encryption keys of the devices. For instance, the programmer may transmit a public encryption key of a public/private key pair of the programmer to the implantable medical device and the implantable medical device (IMD) may similarly transmit a public encryption key of a public/private key pair of the IMD to the programmer. The programmer and IMD may generate a common encryption key based on the public encryption key of the programmer and the public encryption key of the IMD. Following the pairing procedure, the devices may securely communicate using the link encryption key. For instance, the programmer may communicate with the IMD to modify one or more settings of the IMD.

In accordance with one or more techniques of this disclosure, an IMD may selectively operate in the pairing mode of the far-field communications protocol based on a proximity of an external wireless charger of the IMD to the IMD. For instance, in response to determining that the wireless charger has been brought into proximity of the IMD, the IMD may transition from a non-pairing mode into the pairing mode in-which the public key exchange is performed. In other words, when operating in the pairing mode, the IMD may perform the public key exchange to generate the link key to be used for secure communications.

Selectively operating in the pairing mode based on the proximity of the wireless charger to the IMD may provide one or more advantages. For instance, by restricting pairing to a certain time using the deliberate action of introducing the wireless charger to the IMD, the user may ensure that they are in an area in-which they are unlikely to be eavesdropped during the pairing of their external device (e.g., their residence).

As one example, a method includes, responsive to determining that a charging coil of a wireless charger has been brought into proximity of an implantable medical device, transitioning, by the implantable medical device, from a non-pairing mode into a pairing mode of a far-field wireless communication protocol. In this example, operating in the paring mode includes: receiving, by the implantable medical device and via a transceiver of the far-field wireless communication protocol, a public encryption key from another device that is different than the wireless charger; and determining, based on the public encryption key of the other device and a public encryption key of the implantable medical device, a link encryption key for future communication between the implantable medical device and the other device. In this example, the method also includes communicating, by the implantable medical device and based on the link encryption key, with the other device via the far-field wireless communication protocol.

As another example, an implantable medical device includes a wireless transceiver configured to operate in accordance with a far-field wireless communication protocol; and one or more processors. In this example, the one or more processors are configured to: transition, responsive to determining that a charging coil of a wireless charger has been brought into proximity of the implantable medical device, from operating in a non-pairing mode into a pairing mode of the far-field wireless communication protocol. In this example, when operating in the pairing mode, the one or more processors are configured to: receive, via the transceiver, a public encryption key from another device that is different than the wireless charger; and determine, based on the public encryption key of the other device and a public encryption key of the implantable medical device, a link encryption key for future communication between the implantable medical device and the other device. In this example, the one or more processors also configured to communicate, based on the link encryption key, with the other device via the far-field wireless communication protocol.

In another example, a computer-readable storage medium stores instructions that, when executed, cause one or more processors of an implantable medical device to: transition, responsive to determining that a charging coil of a wireless charger has been brought into proximity of an implantable medical device, from operating a non-pairing mode into a pairing mode of a far-field wireless communication protocol. In this example, the instructions that cause the one or more processors to operate in the paring mode comprise instructions that cause the one or more processors to: receive, via a transceiver of the far-field wireless communication protocol, a public encryption key from another device that is different than the wireless charger; and determine, based on the public encryption key of the other device and a public encryption key of the implantable medical device, a link encryption key for future communication between the implantable medical device and the other device. In this example, the computer-readable storage medium further stores instructions that cause the one or more processors to communicate, based on the link encryption key, with the other device via the far-field wireless communication protocol.

In another example, an implantable medical device comprises: means for transitioning, responsive to determining that a charging coil of a wireless charger has been brought into proximity of an implantable medical device, from operation in a non-pairing mode into a pairing mode of a far-field wireless communication protocol; means for operating in the pairing mode that comprise: means for receiving, via a transceiver of the far-field wireless communication protocol, a public encryption key from another device that is different than the wireless charger; and means for determining, based on the public encryption key of the other device and a public encryption key of the implantable medical device, a link encryption key for future communication between the implantable medical device and the other device. In this example, the implantable medical device further comprises means for communicating, based on the link encryption key, with the other device via the far-field wireless communication protocol.

The details of one or more example are set forth in the accompanying drawings and the description below. Other features, objects, and advantages will be apparent from the description and drawings, and from the claims.

DETAILED DESCRIPTION

Figure 1A:
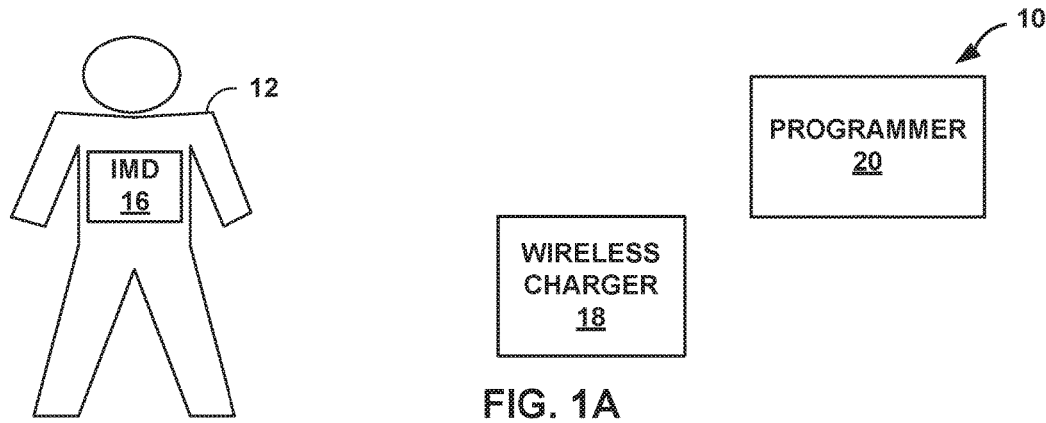
FIGS. 1A-1C are conceptual diagrams illustrating an example therapy system that is configured to deliver therapy to a patient to manage a disorder of the patient, in accordance with one or more aspects of this disclosure.

In general, the disclosure is directed to devices, systems, and techniques for secure wireless communication between two devices (e.g., a medical device programmer or other external device and an implantable medical device) using a far-field communication protocol, such as a Bluetooth communication protocol. Prior to secure communication, the two devices may perform a pairing procedure. The devices may perform the pairing procedure while operating in a pairing mode. During the pairing procedure, the devices may each generate an encryption key (e.g., a link encryption key) based on respective encryption keys of the devices. For instance, the programmer may transmit a public encryption key of a public/private key pair of the programmer to the implantable medical device and the implantable medical device (IMD) may similarly transmit a public encryption key of a public/private key pair of the IMD to the programmer. The programmer and IMD may generate a common encryption key based on the public encryption key of the programmer and the public encryption key of the IMD. Following the pairing procedure, the devices may securely communicate using the link encryption key. For instance, the programmer may communicate with the IMD to modify one or more settings of the IMD.

The devices may exchange the public keys using unencrypted communication, also known as "in the clear" communication. Due to the unencrypted nature of the exchange, the public key exchange may be susceptible to attack, such as a "man-in-the-middle" (MITM) attack, and the security of the following communications may be compromised. A man-in-the-middle (MITM) attack occurs when, instead of connecting two devices directly with each other, the devices unknowingly connect to a third (attacking) device that plays the role of the device they are attempting to pair with. The third device then relays information between the two devices giving the illusion that they are directly connected. The attacking device may even eavesdrop on communication between the two devices (known as active eavesdropping) and may be able to insert and modify information on the connection. In this type of attack, all of the information exchanged between the two devices may be compromised and the attacker may inject commands and information into each of the devices thus potentially damaging the function of the devices. Devices falling victim to the attack are capable of communicating only when the attacker is present. If the attacker is not active or out range, the two victim devices will not be able to communicate directly with each other and the user will notice it.

Several techniques may be available to reduce or eliminate the possibility of an attack on the key exchange and subsequent hijacking of the inter-device communications. Example techniques include passkey entry, numeric comparison, out-of-band, and just works.

Passkey entry may be available in scenarios where one device has input capability but does not have the capability to display a number and the other device has output capabilities. A good example of this model is the PC and keyboard scenario. In passkey entry, a user of the devices is shown a number (e.g., a six-digit number from "000000" to "999999") on the device with a display, and is then asked to enter the number on the other device. If the value entered on the second device is correct, the pairing of the devices proceeds and subsequent secure communication is enabled. Similarly, if the value entered on the second device is not correct, the pairing of the devices does not proceed and subsequent secure communication is not enabled. However, as an IMD may not have input capability (i.e., due to being implanted in a patient), it may not be possible to use passkey entry to reduce or eliminate the possibility of an attack on the key exchange.

Numeric comparison may be available in scenarios where both devices are capable of displaying a number and both are capable of having the user enter "yes" or "no." A good example of this model is the cell phone/PC scenario. In numeric comparison, a user of the devices is shown a number (e.g., a six-digit number from "000000" to "999999") on both displays and then asked whether the numbers are the same on both devices. If "yes" is entered on both devices, the pairing of the devices proceeds and subsequent secure communication is enabled. Similarly, if "yes" is not entered on both devices, the pairing of the devices does not proceed and subsequent secure communication is not enabled. However, as an IMD may not have input capability (i.e., due to being implanted in a patient), it may not be possible to use numeric comparison to reduce or eliminate the possibility of an attack on the key exchange.

Out-of-band (OOB) may be available in scenarios where another communication channel (i.e., in addition to the communication channel being secured) is available on both devices, e.g., to discover the devices as well as to exchange or transfer cryptographic numbers used in the pairing process. In OOB, the other communication channel is used to perform the key exchange or other components of the pairing procedure. To be effective from a security point of view, the other communication channel should provide different properties in terms of security compared to the communication channel being secured. While it may be possible to include the capability to communicate via an additional communication channel in an IMD and a programmer, such inclusion may be undesirable. For instance, in order to communicate over an additional communication channel, the IMD or the other device may require additional hardware, which may undesirably increase the size and/or complexity of the IMD or the other device.

Additionally, even if IMD is already capable of communicating over an additional communication channel (e.g., with a wireless charger of the IMD via near-field communication techniques), the programmer may not be capable of communicating via the additional communication channel. As such, the use of OOB over the additional communication channel would either require modification of the programmer to communicate over the additional communication channel or require an intermediate device to communicate with the IMD over the additional communication channel and with the programmer in some other manner.

Just works may be available in scenarios where at least one of the devices does not have a display capable of displaying a number nor does it have a keyboard capable of entering a number. A good example of this model is the cell phone/mono headset scenario where most headsets do not have a display. Just works operates similarly to the numeric comparison but the user is never shown a number and the application may simply ask the user to accept the connection. For instance, just works may provide the same protection as the numeric comparison association model against passive eavesdropping but offers no protection against MITM attacks. In particular, if an attacking device is within range during the key exchange using just works, the attacking device may successfully perform a MITM attack.

As discussed above, it may not be possible to utilize numeric comparison or passkey entry because the IMD may not be capable of displaying a number, and it may not be desirable to utilize OOB due to the undesirable increase in the size of the IMD. Similarly, it may not be desirable to utilize Just Works due to the lack of protection against MITM attacks. As such, it may be desirable for the devices to utilize a technique that reduces or eliminates the possibility of an attack on the key exchange, does not require the IMD to have a display, does not increase the size of the IMD, and provides some protection against MITM attacks.

In accordance with one or more techniques of this disclosure, an IMD may selectively operate in the pairing mode of the far-field communications protocol based on a proximity of a wireless charger of the IMD. For instance, in response to determining that the wireless charger has been brought into proximity of the IMD (e.g., in response to determining that a charging could of the wireless charger is in proximity), the IMD may transition from a non-pairing mode into the pairing mode in-which the public key exchange is performed. In other words, when operating in the pairing mode, the IMD may perform the public key exchange to generate the link key to be used for secure communications. The IMD may be configured such that, when the wireless charger is not in proximity of the IMD, the IMD does not transition from a non-pairing mode into the pairing mode in-which the public key exchange is performed.

Selectively operating in the pairing mode based on the proximity of the wireless charger may provide one or more advantages. For instance, by restricting pairing to a certain time using the deliberate action of introducing the wireless charger to the IMD, the user may ensure that they are in an area in which they are unlikely to be eavesdropped upon during the pairing of their external device (e.g., the residence or some other controlled environment of a patient).

While described herein as being paired with a programmer, techniques of this disclosure are equally applicable to pairing IMDs with other types of external devices. For instance, techniques of this disclosure may enable pairing of an IMD with interrogation devices, acquisition devices, and any other type of device that may not necessarily program the IMD.

Figure 1B:
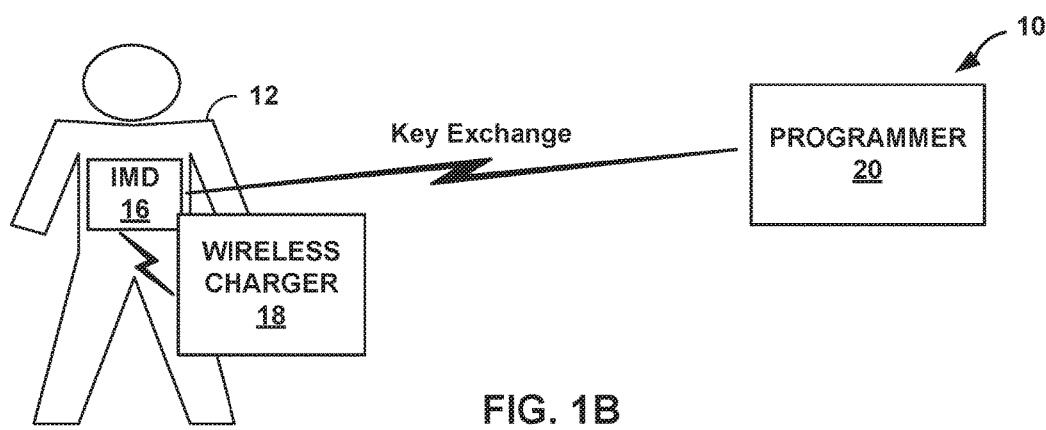
Figure 1C:
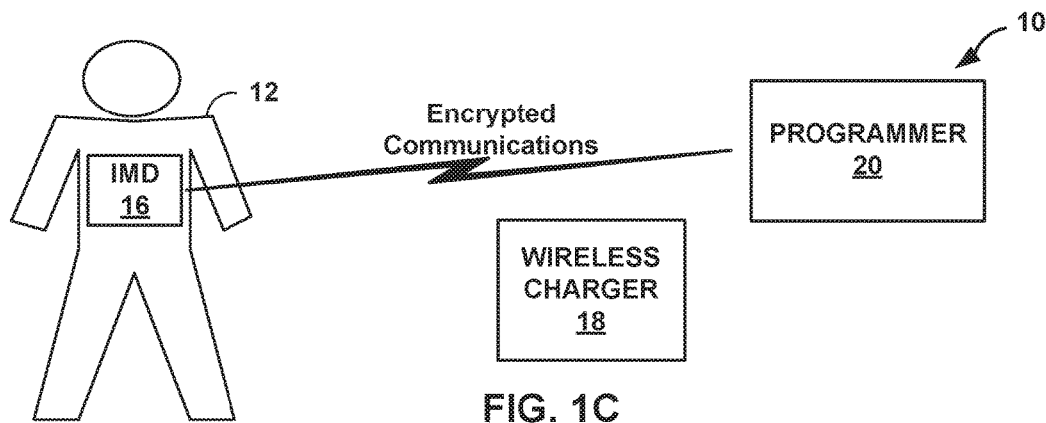

FIGS. 1A-1C are conceptual diagrams illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIGS. 1A-1C, therapy system 10 includes IMD 16, wireless charger 18, and programmer 20.

In the example of FIGS. 1A-1C, IMD 16 is an implantable electrical stimulator that delivers neurostimulation therapy to patient 12, e.g., for relief of chronic pain or other symptoms such as abnormal movements. Generally IMD 16 may be a chronic electrical stimulator (or a device that chronically delivers a pharmacological agent to a patient (e.g., a drug pump device)) that remains implanted within patient 12 for weeks, months, or even years. In the example of FIGS. 1A-1C, IMD 16 may be directed to delivering electrical stimulation therapy. In other examples, IMD 16 may be a temporary, or trial, stimulator used to screen or evaluate the efficacy of electrical stimulation or drug delivery for chronic therapy. IMD 16 may be implanted in a subcutaneous tissue pocket, within one or more layers of muscle, or other internal location within the body of patient 12.

IMD 16 may be configured to generate and deliver electrical stimulation energy, which may be constant current or constant voltage based pulses, for example, that is delivered from IMD 16 to one or more targeted locations within patient 12 via one or more electrodes (not shown). The therapy parameters for a program that controls delivery of stimulation energy by IMD 16 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example. Programmer 20 may be configured to transmit these programs, therapy parameters, and/or adjustments to therapy parameters to IMD 16. In addition to being configured to deliver therapy to manage a disorder of patient 12, therapy system 10 may be configured to sense bioelectrical brain signals or another physiological parameter of patient 12.

IMD 16 may include an on-board battery or other power storage device configured to provide electrical power to one or more components of IMD 16. While the on-board battery may power the medical device for a relatively long period of time, the on-board battery will eventually be depleted. Prior to rechargeable medical systems, the implantable medical device would be replaced once the battery became depleted. With rechargeable medical systems, an external device may provide recharge energy over a proximity coupling, which is typically inductive, to IMD 16. For example, as shown in FIG. 1B, wireless charger 18 may brought into proximity of IMD 16 in order to recharge the battery of IMD 16 to a satisfactory level for continued operation of IMD 16.

Wireless charger 18 may include a charging coil and a controller that may control the amount of power provided by the charging coil. In some examples, the controller and the charging coil may be included in a common housing. For instance, as shown in the example of FIGS. 1A-1C, the controller and the charging coil of wireless charger 18 may be included in a common housing. In some examples, the controller and the charging coil may be in different housings. For instance, the charging coil may be tethered to the controller via a cable/cord. In either case, the coil may be configured to transcutaneously transfer energy to a charging coil of IMD 16. For instance, the charging coil of wireless charger 18 may transcutaneously induce a current in the charging coil of IMD 16.

External medical device programmer 20 is configured to wirelessly communicate with IMD 16 as needed to provide or retrieve therapy information. Programmer 20 is an external computing device that the user, e.g., the clinician and/or patient 12, may use to communicate with IMD 16. For example, programmer 20 may be a clinician programmer that the clinician uses to communicate with IMD 16 and program one or more therapy programs for IMD 16. In addition, or instead, programmer 20 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 20 may be a hand-held computing device with a display viewable by the user and an interface for providing input to programmer 20 (i.e., a user input mechanism). For example, programmer 20 may include a small display screen (e.g., a liquid crystal display (LCD) or a light emitting diode (LED) display) that presents information to the user. In addition, programmer 20 may include a touch screen display, keypad, buttons, a peripheral pointing device, voice activation, or another input mechanism that allows the user to navigate through the user interface of programmer 20 and provide input. If programmer 20 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 20 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 20. A wireless adapter coupled to the computing device may enable secure communication between the computing device and IMD 16.

When programmer 20 is configured for use by the clinician, programmer 20 may be used to transmit programming information to IMD 16. Programming information may include, for example, hardware information, such as the type of leads used, the arrangement of electrodes on the leads, the position of the leads within the brain, one or more therapy programs defining therapy parameter values, therapeutic windows for one or more of the electrodes, and any other information that may be useful for programming into IMD 16.

The clinician may also generate and store therapy programs within IMD 16 with the aid of programmer 20. Programmer 20 may assist the clinician in the creation/identification of therapy programs by providing a system for identifying potentially beneficial therapy parameter values. For example, during a programming session, programmer 20 may automatically select a combination of electrodes for delivery to therapy to the patient. In some examples, at least some of the therapy programs may have the same electrode combination (but different values of at least one other therapy parameter) and these therapy programs may be organized into subsets, each subset having the same electrode combination. A processor of programmer 20 may select the most efficacious therapy program for each subset and display a list of the selected therapy programs. The clinician may select a therapy program from the list to provide therapy to patient 12 to address symptoms associated with the patient condition.

Programmer 20 may also be configured for use by patient 12. When configured as a patient programmer, programmer 20 may have limited functionality (compared to a clinician programmer) in order to prevent patient 12 from altering critical functions of IMD 16 or applications that may be detrimental to patient 12.

Whether programmer 20 is configured for clinician or patient use, programmer 20 is configured to communicate with IMD 16 and, optionally, another computing device, via wireless communication. Programmer 20, for example, may communicate via near-field communication technologies (e.g., inductive coupling, Near-field Communication (NFC) or other communication technologies operable at ranges less than 10-20 centimeters) and far-field communication technologies (e.g., as radiofrequency (RF) telemetry according to the 802.11 or Bluetooth specification sets, or other communication technologies operable at ranges greater than near-field communication technologies).

Communications (e.g., information or data) transmitted between programmer 20 and IMD 16 may be encrypted to secure the communications from unauthenticated users and prevent programmer 20 and IMD 16 from becoming compromised. For instance, communications transmitted between programmer 20 and IMD 16 using a far-field communication protocol may be encrypted using a link key that is generated based on public encryption keys of programmer 20 and IMD 16. As discussed above, programmer 20 and IMD 16 may exchange the public encryption keys via transceivers of the far-field communications protocol while operating in a pairing mode.

In accordance with one or more techniques of this disclosure, IMD 16 may selectively operate in the pairing mode of the far-field communications protocol based on a proximity of wireless charger 18 to IMD 16. For instance, as shown in FIG. 1B, in response to determining that wireless charger 18 (e.g., a charging coil of wireless charger 18) has been brought into proximity of IMD 16, IMD 16 may transition from a non-pairing mode into the pairing mode in-which the public key exchange is performed. In particular, IMD 16 may output a public key of a public/private key pair to programmer 20 In other words, when operating in the pairing mode, the IMD may perform the public key exchange to generate the link key to be used for secure communications.

Selectively operating in the pairing mode based on the proximity of the wireless charger may provide one or more advantages. For instance, by restricting pairing to a certain time using the deliberate action of introducing the wireless charger to the IMD, the user may ensure that they are in an area in-which they are unlikely to be eavesdropped during the pairing of their external device (e.g., their residence).

After the encryption keys are generated in each of programmer 20 and IMD 16, secure communications may commence. For example, programmer 20 may encrypt programming instructions for IMD 16 using the encryption key generated by the programmer and transmit the encrypted communications to IMD 16. IMD 16 may then use the matching encryption key generated by IMD to decrypt the instructions. Similarly, IMD 16 may send encrypted communications to programmer 20. As shown in FIG. 1C, after successful pairing, wireless charger 18 need not remain in proximity to IMD 16 in order for programmer 20 and IMD 16 to exchange encrypted communications.

Figure 2:
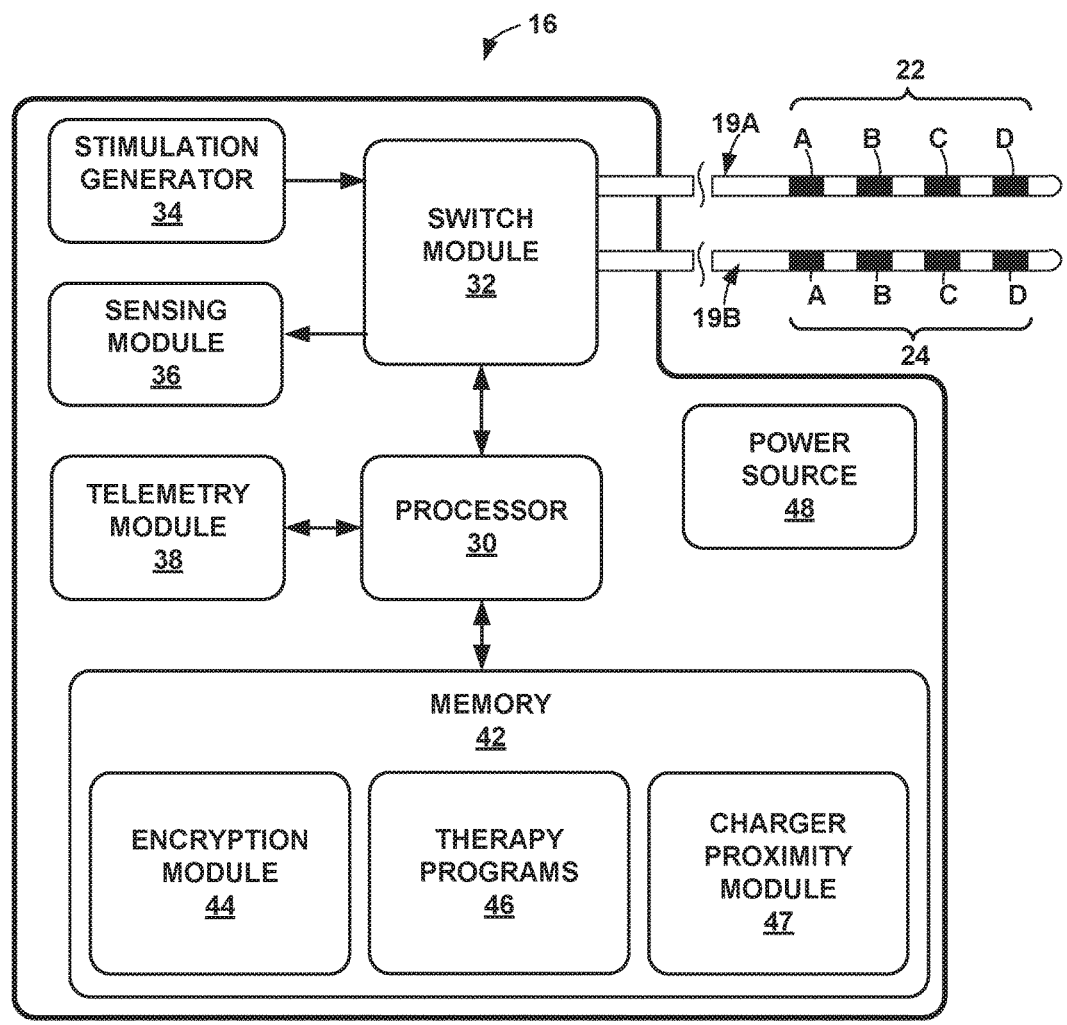
FIG. 2 is a block diagram of an example implantable medical device (IMD) for delivering electrical stimulation therapy and generating encryption keys, in accordance with one or more aspects of this disclosure.

FIG. 2 is a block diagram of example IMD 16 of FIGS. 1A-1C for delivering electrical stimulation therapy and generating encryption keys. In the example shown in FIG. 2, IMD 16 includes processor 30, memory 42, stimulation generator 34, sensing module 36, switch module 32, telemetry module 38, and power source 48. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 30, cause IMD 16 to perform various functions, such as delivering stimulation therapy and generating encryption keys. Memory 42 may be a storage device or other non-transitory medium.

In the example shown in FIG. 2, memory 42 stores, among other data, therapy programs 46 and encryption module 44 in separate memories within memory 42 or separate areas within memory 42. In some cases, encryption module 44 and/or any encryption keys may be firewalled from various components, such as telemetry module 38, to reduce the likelihood of an unauthorized user from obtaining encryption keys or other encryption information. Each stored therapy program 46 defines a particular set of electrical stimulation parameters (e.g., a therapy parameter set) and corresponding parameter values, such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Charger proximity module 47 may include instructions that cause processor 30 to determine whether a wireless charger (e.g., wireless charger 18) has been brought into proximity of IMD 16. As one example, charger proximity module 47 may determine that the wireless charger has been brought into proximity of IMD 16 in response to determining that IMD 16 is receiving power from the wireless charger. For instance, charger proximity module 47 may be executable by processor 30 to determine whether IMD 16 is receiving power from a charging coil of wireless charger 18 based on detection of induced current on of a charging coil of IMD 16, a voltage across a load of IMD 16 (e.g., a battery of IMD 16 and/or a battery charger of IMD 16), or power delivered to a load of IMD 16.

As another example, charger proximity module 47 may determine that the wireless charger has been brought into proximity of IMD 16 in response to determining that a distance between IMD 16 and the wireless charger is less than a threshold distance (e.g., 1 centimeter, 5 centimeters, 10 centimeters, 20 centimeters, 50 centimeters, etc.).

Encryption module 44 may include instructions that cause processor 30 and/or another processor (e.g., a dedicated encryption module configured to perform encryption tasks described herein) to generate encryption keys (such as link keys) using public encryption keys of IMD 16 and another device. Encryption module 44 may include instructions that cause processor 30 and/or another processor to store the generated encryption keys for future use (e.g., in memory 42). IMD 16 may receive encryption module 44 during manufacture or otherwise prior to being implanted in patient 12 to maintain security of the encryption instructions. In some examples, IMD 16 may receive updates to encryption module 44 after IMD 16 has been implanted in patient 12.

As discussed above and in accordance with one or more techniques of this disclosure, IMD 16 may selectively operate in the pairing mode of a far-field communications protocol based on a proximity of wireless charger 18 to IMD 16. For instance, charger proximity module 47 may determine whether a wireless charger is in proximity of IMD 16. Responsive to determining that the wireless charger has been brought into proximity of IMD 16, charger proximity module 47 outputs a notification to encryption module 44 indicating as such.

Responsive to receiving the notification from charger proximity module 47 that the wireless charger has been brought into proximity of IMD 16, encryption module 44 may transition into a pairing mode. While operating in the pairing mode, encryption module 44 may exchange public encryption keys with another device. For instance, encryption module 44 may receive, from another device that is different than the wireless charger and via a transceiver of telemetry module 38 associated with the far-field wireless communication protocol, a public encryption key of the other device. Encryption module 44 may similarly transmit, to the other device and via the transceiver of telemetry module 38 associated with the far-field wireless communication protocol, a public encryption key of IMD 16.

Encryption module 44 may determine, based on the public encryption key of the other device and a public encryption key of IMD 16, a link encryption key for future communication between IMD 16 and the other device. For instance, where the far-field communication protocol is a Bluetooth communication protocol, encryption module 44 may exchange the public encryption keys and determine the link encryption key in accordance with the Bluetooth communication protocol. "Bluetooth Core Specification v5.0," Bluetooth Special Interest Group (SIG), Adopted Dec. 6, 2016 is available at bluetooth.org/DocMan/handlers/DownloadDoc.ashx?doc_id=421043.

Stimulation generator 34, under the control of processor 30, is configured to generate stimulation signals for delivery to patient 12 via selected combinations of electrodes 22, 24. Lead 19A includes electrodes 22A, 22B, 22C, and 22D (collectively "electrodes 22). Lead 19B includes electrodes 24A, 24B, 24C, and 24D (collectively "electrodes 24"). Leads 19A and 19B (collectively "leads 19") may include fewer or greater than four electrodes each. Accordingly, in some examples, stimulation generator 34 generates electrical stimulation signals in accordance with various electrical stimulation parameters appropriate for SCS or some other therapy selected to treat one or more conditions of patient 12. Therapy programs, therapy parameter values, and other instructions that define therapy delivery may be selected by the clinician, patient 12, and/or updated over time. While stimulation pulses are generally described, stimulation signals may be of any form, such as continuous-time signals (e.g., sine waves) or the like.

Processor 30 may include any one or more of a microprocessor, a controller, a digital signal processor (DSP), an application specific integrated circuit (ASIC), a field-programmable gate array (FPGA), discrete logic circuitry, and the functions attributed to processor 30 herein may be embodied as firmware, hardware, software or any combination thereof. Processor 30 controls stimulation generator 34 according to therapy programs 46 stored in memory 42 to apply particular stimulation parameter values specified by one or more of programs, such as amplitude, pulse width, and pulse rate.

In the example shown in FIG. 2, the set of electrodes 22 and 24 can be used to deliver electrical stimulation to patient 12. Processor 30 also controls switch module 32 to apply the stimulation signals generated by stimulation generator 34 to selected combinations of electrodes 22, 24. In particular, switch module 32 may couple stimulation signals to selected conductors within leads 19, which, in turn, deliver the stimulation signals across selected electrodes 22, 24. Switch module 32 may be a switch array, switch matrix, multiplexer, or any other type of switching module configured to selectively couple stimulation energy to selected electrodes 22, 24. Hence, stimulation generator 34 is coupled to electrodes 22, 24 via switch module 32 and conductors within leads 19. In some examples, however, IMD 16 does not include switch module 32.

Stimulation generator 34 may be a single channel or multi-channel stimulation generator. In particular, stimulation generator 34 may be capable of delivering a single stimulation pulse, multiple stimulation pulses, or a continuous signal at a given time via a single electrode combination or multiple stimulation pulses at a given time via multiple electrode combinations. Although sensing module 36 is incorporated into a common housing with stimulation generator 34 and processor 30 in FIG. 2, in other examples, sensing module 36 may be in a separate housing from IMD 16 and may communicate with processor 30 via wired or wireless communication techniques.

Telemetry module 38 supports wireless communication between IMD 16 and external programmer 20 or another computing device under the control of processor 30. Processor 30 of IMD 16 may receive instructions from programmer 20 via telemetry module 38. For example, processor 30 may receive, e.g., as updates to programs, values for various stimulation parameters such as amplitude and electrode combination, from programmer 20 via telemetry module 38. Some or all of these communications from programmer 20 may be encrypted using an encryption key generated by programmer 20 and matching the encryption key generated by IMD 16. The updates to the therapy programs may be stored within therapy programs 46 portion of memory 42. IMD 16 may also transmit, via telemetry module 38, encrypted information (e.g., sensed patient data or operational information of IMD 16) to programmer 20. Telemetry module 38 in IMD 16, as well as telemetry modules in other devices and systems described herein, such as programmer 20, may accomplish communication by radiofrequency (RF) communication techniques. In addition, telemetry module 38 may communicate with external medical device programmer 20 via proximal inductive interaction of IMD 16 with programmer 20. Accordingly, telemetry module 38 may send information to external programmer 20 on a continuous basis, at periodic intervals, or upon request from IMD 16 or programmer 20.

Power source 48 delivers operating power to various components of IMD 16. Power source 48 may include a small rechargeable or non-rechargeable battery and a power generation circuit to produce the operating power. Recharging may be accomplished through proximal inductive interaction between an external charger, such as wireless charger 18, and an inductive charging coil within IMD 16.

Figure 3:
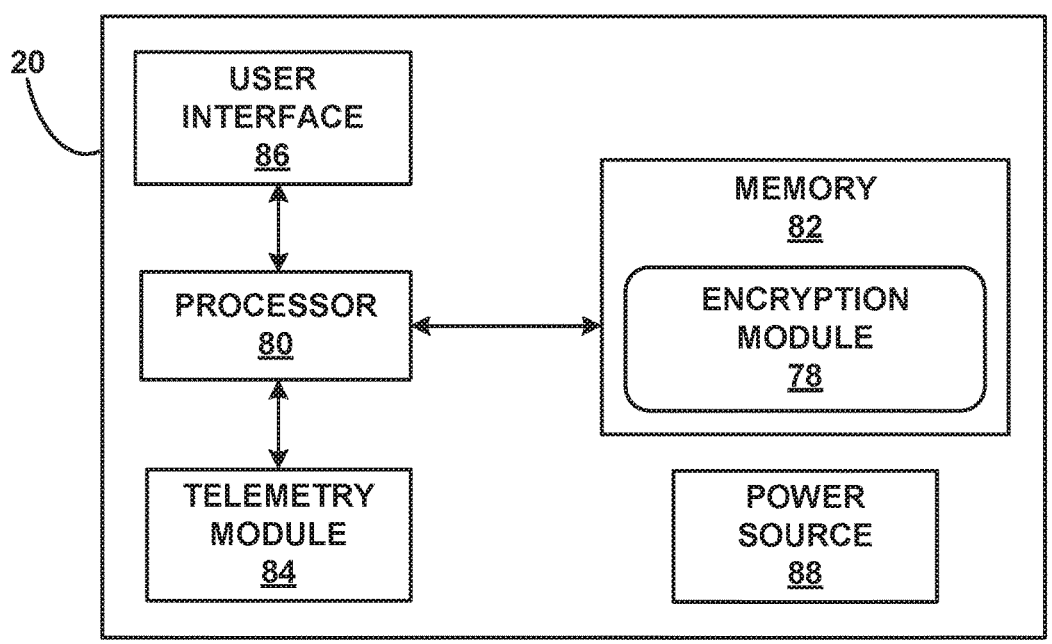
FIG. 3 is a functional block diagram illustrating components of an example medical device programmer for an IMD, in accordance with one or more aspects of this disclosure.

FIG. 3 is a functional block diagram illustrating components of an example medical device programmer 20 (FIGS. 1A-1C). Programmer 20 includes processor 80, memory 82, telemetry module 84, user interface 86, and power source 88. Processor 80 controls user interface 86 and telemetry module 84, and stores and retrieves information and instructions to and from memory 82. Programmer 20 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 20 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 80 of programmer 20 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores instructions and/or data associated with encryption module 78.

In some examples, patient 12, a clinician or another user may interact with user interface 86 of programmer 20 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 20 is used by a different patient.

Wireless telemetry in programmer 20 may be accomplished by RF communication. This wireless communication is possible through the use of telemetry module 84. Accordingly, telemetry module 84 may be similar to the telemetry module contained within IMD 16. In other examples, programmer 20 may be capable of infrared communication or direct communication through a wired connection. In this manner, other external devices may be capable of communicating with programmer 20 without needing to establish a secure wireless connection.

Power source 88 is configured to deliver operating power to the components of programmer 20. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 20. In other examples, traditional batteries (e.g., nickel cadmium or lithium ion batteries) may be used. In addition, programmer 20 may be directly coupled to an alternating current outlet to operate.

Encryption module 78 may be configured to perform operations similar to encryption module 44 of IMD 16. For instance, encryption module 78 may include instructions that cause processor 80 and/or another processor (e.g., a dedicated encryption module configured to perform encryption tasks described herein) to generate encryption keys (such as link keys) using public encryption keys of programmer 20 and another device, such as IMD 16. Encryption module 78 may include instructions that cause processor 80 and/or another processor to store the generated encryption keys for future use (e.g., in memory 82). In some examples, encryption module 78 may include instructions that cause processor 80 and/or another processor to exchange public encryption keys and generate link keys in accordance with a Bluetooth communication protocol.

Figure 4:
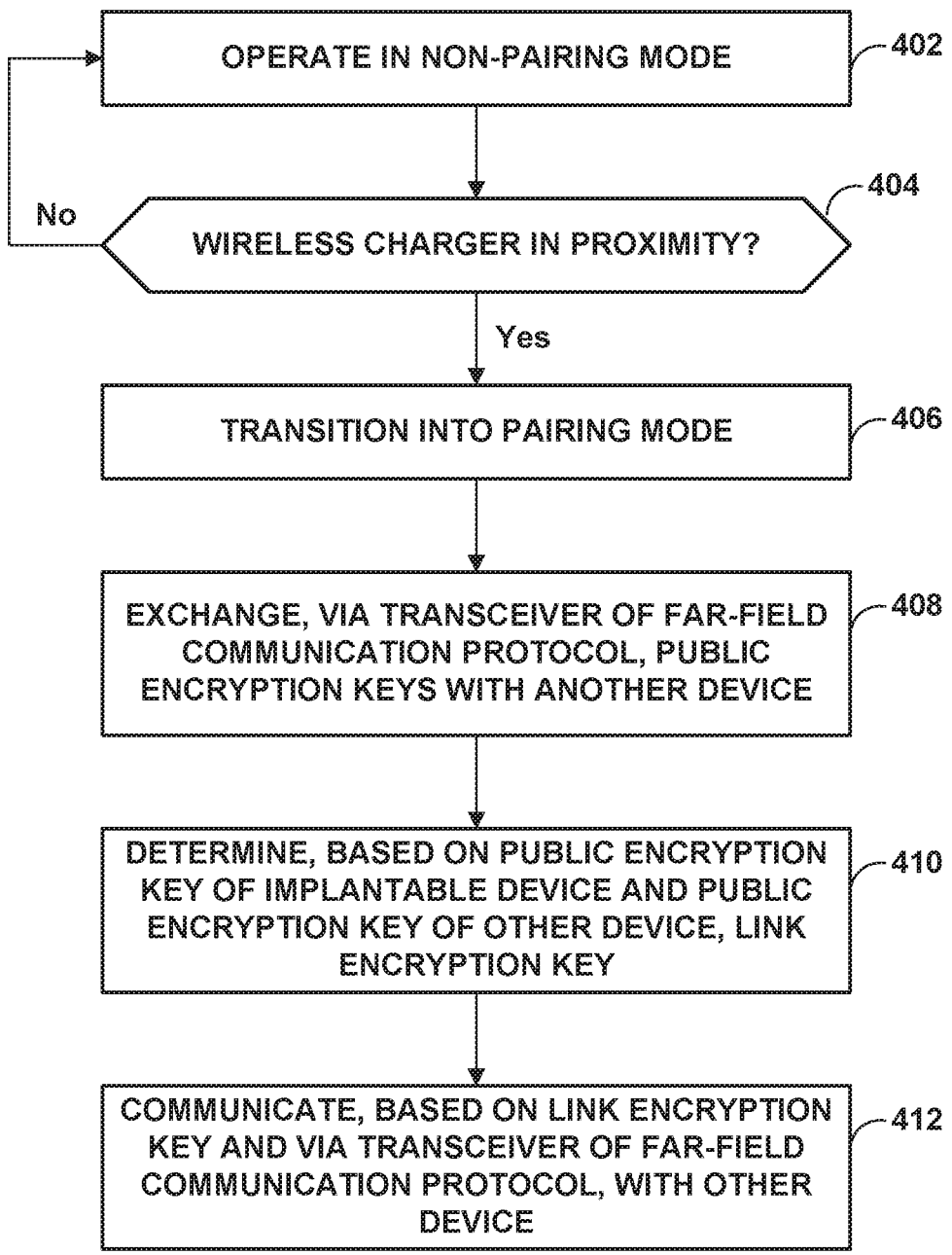
FIG. 4 is a flow diagram illustrating an example process for selectively pairing an implantable medical device (IMD) with an external device such as a programmer based on proximity of a wireless charger to the IMD, in accordance with one or more techniques of this disclosure.

FIG. 4 is a flow diagram illustrating an example process for selectively pairing an implantable medical device based on proximity of a wireless charger, in accordance with one or more techniques of this disclosure. Although FIG. 4 will be described with respect to processor 30 of IMD 16, similar processes would be performed by processor 80 and programmer 20, or the other device with which IMD 16 is to be bonded to generate matching encryption keys. Other sets of devices may also be used in other examples.

Initially, IMD 16 may operate in a non-pairing mode of a far-field wireless communication protocol (402). In the non-pairing mode, IMD 16 may refrain from exchanging public keys with any other devices. In some examples, IMD 16 may remain discoverable to other devices while operating in the non-pairing mode. For instance, IMD 16 may remain discoverable such that devices that are bonded with IMD 16 (i.e., devices that have previously paired with IMD 16) may exchange encrypted communications with IMD 16 via the far-field communication protocol. As discussed above, in some examples, the far-field communication protocol may be a Bluetooth communication protocol.

IMD 16 may determine whether a wireless charger has been brought into proximity of IMD 16 (404). For instance, charger proximity module 47 of IMD 16 may be executable by processor 30 of IMD 16 to determine whether IMD 16 is receiving power from a charging coil of wireless charger 18 of FIGS. 1A-1C. In some examples, charger proximity module 47 of IMD 16 may be executable by processor 30 of IMD 16 to determine whether IMD 16 is receiving power from a charging coil of wireless charger 18 based on detection of induced current on of a charging coil of IMD 16, a voltage across a load of IMD 16 (e.g., a battery of IMD 16 and/or a battery charger of IMD 16), or power delivered to a load of IMD 16. If the wireless charger has not been brought into proximity of IMD 16 ("No" branch of 404), IMD 16 may remain in the non-pairing mode (402).

If the wireless charger has been brought into proximity of IMD 16 ("Yes" branch of 404), IMD 16 may transition into a pairing mode of the far-field wireless communication protocol (406). In some examples, IMD 16 may operate in the pairing mode for a predetermined amount of time (e.g., 30 seconds, 1 minute, 5 minutes, 10 minutes, etc.) before transitioning into the non-pairing mode. In some examples, IMD 16 may operate in the pairing mode for the predetermined amount of time before transitioning into the non-pairing mode regardless of the proximity of the wireless charger to IMD 16. For instance, IMD 16 may operate in the pairing mode for the predetermined amount of time before transitioning into the non-pairing mode even if IMD 16 is ceases to receive power from the wireless charger. In some examples, IMD 16 may transition from the pairing mode into the non-pairing mode responsive to determining that the charging coil is no longer in proximity of IMD 16 (e.g., not in proximity of IMD 16).

In any case, while operating in the pairing mode, IMD 16 may be operable to pair with another device using the Just Works association model described above. For instance, IMD 16 may exchange, via a transceiver of the far-field communication protocol, public encryption keys with another device (408). In some examples, to exchange the encryption keys, encryption module 44 of IMD 16 may be executable by processor 30 to transmit, via a far-field transmitter of telemetry module 38, a public encryption key of IMD 16 to programmer 20 of FIGS. 1A-1C. Encryption module 44 of IMD 16 may also be executable by processor 30 to receive, via a far-field receiver of telemetry module 38, a public encryption key of programmer 20.

IMD 16 may determine, based on the received public encryption key of the other device and the public encryption key of IMD 16, a link encryption key for future communication between IMD 16 and the other device (410). In some examples, IMD 16 and the other device may verify that the link encryption key determined by IMD 16 matches a link encryption key generated by the other device. In some examples, once the devices determine that the link encryption keys match, the devices may be considered to be bonded and may communicate in the future without again performing the pairing procedure (i.e., so long as neither device deletes the link encryption key).

IMD 16 and the other device may communicate, based on the link encryption key and via the transceiver of the far-field communication protocol (412).

While the techniques described above are primarily described as being performed by processor 30 of IMD 16 or processor 80 of programmer 20, in other examples, one or more other processors may perform any part of the techniques described herein alone or in addition to processor 30 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other embodiments are within the scope of the following claims.

What is claimed is:

1. A method comprising:
responsive to determining that a charging coil of a wireless charger is in proximity of an implantable medical device, transitioning, by the implantable medical device, from a non-pairing mode into a pairing mode of a far-field wireless communication protocol, wherein operating in the pairing mode comprises:
receiving, by the implantable medical device and via a transceiver of the far-field wireless communication protocol, a public encryption key from another device that is different than the wireless charger; and
determining, based on the public encryption key of the other device and a public encryption key of the implantable medical device, a link encryption key for future communication between the implantable medical device and the other device, the method further comprising:
communicating, by the implantable medical device and based on the link encryption key, with the other device via the far-field wireless communication protocol.

2. The method of claim 1, wherein operating in the pairing mode comprises:
operating in the pairing mode for a predetermined amount of time before transitioning into the non-pairing mode.

3. The method of claim 2, wherein operating in the pairing mode for the predetermined amount of time before transitioning into the non-pairing mode comprises:
operating, regardless of the proximity of the charging coil of the wireless charger to the implantable medical device, in the pairing mode for the predetermined amount of time before transitioning into the non-pairing mode.

4. The method of claim 1, further comprising:
responsive to determining that the charging coil of the wireless charger is not in proximity of the implantable medical device, transitioning, by the implantable medical device, into the non-pairing mode.

5. The method of claim 1, wherein the wireless communication protocol comprises a Bluetooth wireless communication protocol.

6. The method of claim 1, wherein determining that the charging coil of the wireless charger is in proximity of the implantable medical device comprises:
determining that the implantable medical device is receiving power from the charging coil of the wireless charger.

7. An implantable medical device comprising:
a wireless transceiver configured to operate in accordance with a far-field wireless communication protocol; and
one or more processors configured to:
transition, responsive to determining that a charging coil of a wireless charger is in proximity of the implantable medical device, from operating in a non-pairing mode into a pairing mode of the far-field wireless communication protocol in which the one or more processors are configured to:
receive, via the transceiver, a public encryption key from another device that is different than the wireless charger; and determine, based on the public encryption key of the other device and a public encryption key of the implantable medical device, a link encryption key for future communication between the implantable medical device and the other device, the one or more processors further configured to:
communicate, based on the link encryption key, with the other device via the far-field wireless communication protocol.

8. The implantable medical device of claim 7, wherein the one or more processors are configured to operate in the pairing mode for a predetermined amount of time before transitioning into the non-pairing mode.

9. The implantable medical device of claim 8, wherein the one or more processors are configured to operate in the pairing mode for the predetermined amount of time before transitioning into the non-pairing mode regardless of the proximity of the charging coil of the wireless charger to the implantable medical device.

10. The implantable medical device of claim 7, wherein, responsive to determining that the charging coil of the wireless charger is not in proximity of the implantable medical device, the one or more processors are configured to transition from operating in the pairing mode into the non-pairing mode.

11. The implantable medical device of claim 7, wherein the wireless communication protocol comprises a Bluetooth wireless communication protocol.

12. The implantable medical device of claim 7, wherein the one or more processors are configured to determine that the charging coil of the wireless charger has been brought into proximity of the implantable medical device in response to determining that the implantable medical device is receiving power from the charging coil of the wireless charger.

13. A non-transitory computer-readable storage medium storing instructions that, when executed, cause one or more processors of an implantable medical device to:
transition, responsive to determining that a charging coil of a wireless charger is in proximity of an implantable medical device, from operating in a non-pairing mode into a pairing mode of a far-field wireless communication protocol, wherein the instructions that cause the one or more processors to operate in the paring mode comprise instructions that cause the one or more processors to:
receive, via a transceiver of the far-field wireless communication protocol, a public encryption key from another device that is different than the wireless charger; and
determine, based on the public encryption key of the other device and a public encryption key of the implantable medical device, a link encryption key for future communication between the implantable medical device and the other device, further comprising instructions that cause the one or more processors to:
communicate, based on the link encryption key, with the other device via the far-field wireless communication protocol.

14. The non-transitory computer-readable storage medium of claim 13, wherein the instructions that cause the one or more processors to transition in the pairing mode comprise instructions that cause the one or more processors to operate in the pairing mode for a predetermined amount of time before transitioning into the non-pairing mode.

15. The non-transitory computer-readable storage medium of claim 14, wherein instructions that cause the one or more processors to operate in the pairing mode for the predetermined amount of time before transitioning into the non-pairing mode comprise instructions that cause the one or more processors to operate in the pairing mode for the predetermined amount of time before transitioning into the non-pairing mode regardless of the proximity of the charging coil of the wireless charger to the implantable medical device.

16. The non-transitory computer-readable storage medium of claim 13, wherein the instructions that cause the one or more processors to transition in the pairing mode comprise instructions that cause the one or more processors to transition from operating in the pairing mode into the non-pairing mode in response to determining that the charging coil of the wireless charger is not in proximity of the implantable medical device.

17. The non-transitory computer-readable storage medium of claim 13, wherein the wireless communication protocol comprises a Bluetooth wireless communication protocol.

18. The non-transitory computer-readable storage medium of claim 13, further comprising instructions that cause the one or more processors to:
determine that the charging coil of the wireless charger has been brought into proximity of the implantable medical device in response to determining that the implantable medical device is receiving power from the charging coil of the wireless charger.

19. An implantable medical device comprising:
means for transitioning, responsive to determining that a charging coil of a wireless charger is in proximity of the implantable medical device, the implantable medical device from operation in a non-pairing mode into a pairing mode of a far-field wireless communication protocol;
means for operating the implantable medical device in the pairing mode that comprise:
means for receiving, via a transceiver of the far-field wireless communication protocol, a public encryption key from another device that is different than the wireless charger; and
means for determining, based on the public encryption key of the other device and a public encryption key of the implantable medical device, a link encryption key for future communication between the implantable medical device and the other device, the implantable medical device further comprising:
means for communicating, based on the link encryption key, with the other device via the far-field wireless communication protocol.

20. The implantable medical device of claim 19, wherein the means for operating the implantable medical device in the pairing mode further comprise:
means for operating the implantable medical device in the pairing mode for the predetermined amount of time before transitioning into the non-pairing mode regardless of the proximity of the charging coil of the wireless charger to the implantable medical device.

* * * * *